United States Patent
Petrick et al.

(10) Patent No.: US 6,798,864 B2
(45) Date of Patent: Sep. 28, 2004

(54) METHODS AND APPARATUS FOR PROVIDING SIGNAL DEPENDENT OFFSET AND GAIN ADJUSTMENTS FOR A SOLID STATE X-RAY DETECTOR

(75) Inventors: Scott William Petrick, Sussex, WI (US); Rowland Frederick Saunders, Hartland, WI (US); Richard Gordon Cronce, New Berlin, WI (US); Jeffrey Alan Kautzer, Pewaukee, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 314 days.

(21) Appl. No.: 10/063,181

(22) Filed: Mar. 28, 2002

(65) Prior Publication Data

US 2003/0185342 A1 Oct. 2, 2003

(51) Int. Cl.⁷ ................................................. H05G 1/64
(52) U.S. Cl. ................ 378/98.8; 378/98.11; 378/98.12; 378/207; 250/208.1
(58) Field of Search ....................... 378/19, 98.8, 98.11, 378/98.12, 207; 250/208.1, 370.09, 370.11

(56) References Cited

U.S. PATENT DOCUMENTS

| | | | |
|---|---|---|---|
| 5,331,682 A | * | 7/1994 | Hsieh ............................ 378/19 |
| 5,352,884 A | | 10/1994 | Petrick et al. ............ 250/208.1 |
| 5,604,347 A | | 2/1997 | Petrick et al. ............ 250/252.1 |

* cited by examiner

Primary Examiner—David V. Bruce
Assistant Examiner—Courtney Thomas
(74) Attorney, Agent, or Firm—McAndrews, Held & Malloy, Ltd.; Peter J. Vogel; Michael A. Dellapenna

(57) ABSTRACT

Methods and apparatus are provided in a diagnostic X-ray system for reducing signal conversion time for a solid-state detector panel of the X-ray system in order to increase frame rate. A measurement of a set of induced signal offsets caused by time varying charge retention associated with the detector panel is performed during a phantom time segment prior to normal signal readout of the detector panel for a current image frame. A set of adjustment values is generated in response to the set of induced signal offsets. Subsets of signal values of the detector panel are read out to a predetermined signal dynamic range as part of normal signal readout of the detector panel in response to the set of adjustment values, thus generating a set of normalized detector signals.

28 Claims, 7 Drawing Sheets

FIG. 4
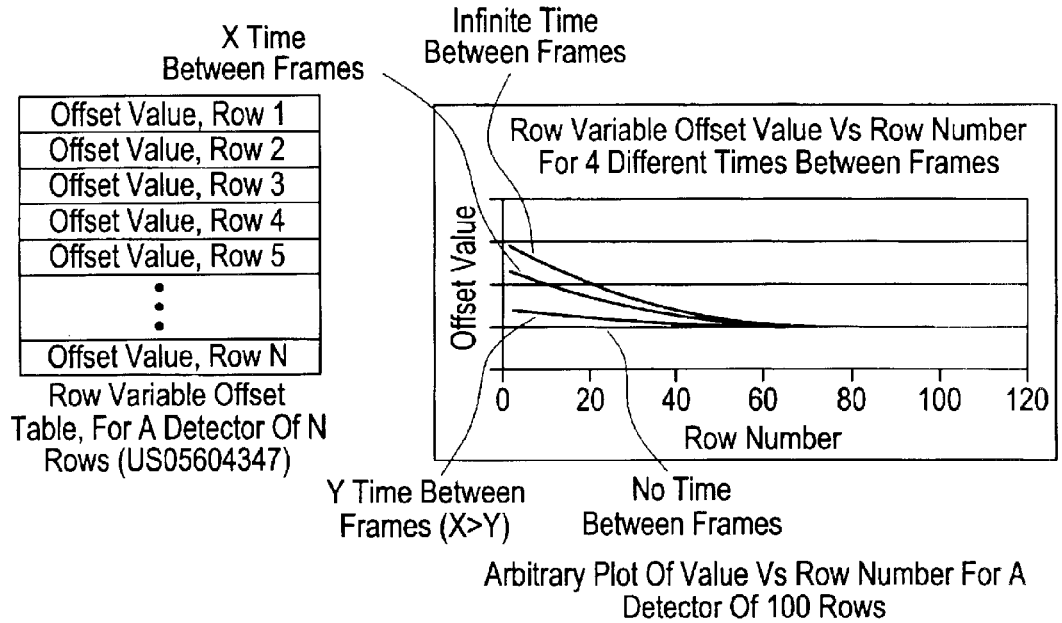
Row Variable Offset Table, For A Detector Of N Rows (US05604347)
Arbitrary Plot Of Value Vs Row Number For A Detector Of 100 Rows
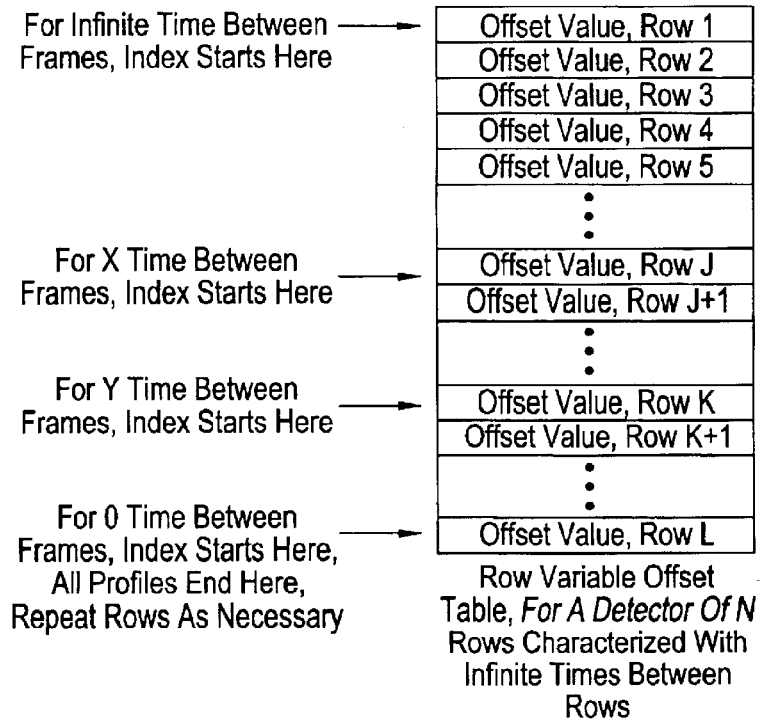
Row Variable Offset Table, *For A Detector Of N* Rows Characterized With Infinite Times Between Rows

METHODS AND APPARATUS FOR PROVIDING SIGNAL DEPENDENT OFFSET AND GAIN ADJUSTMENTS FOR A SOLID STATE X-RAY DETECTOR

BACKGROUND OF INVENTION

Certain embodiments of the present invention relate to a diagnostic X-ray system which measures and images anatomical structures. More particularly, certain embodiments relate to methods and apparatus to reduce signal conversion time for a solid-state panel of the X-ray system in order to increase frame rate.

Within the field of diagnostic X-ray imaging, large area solid-state X-ray detectors have been developed in the X-ray art. Such a detector typically comprises a scintillating layer in contact with an array or panel of photodiodes, each with an associated field-effect transistor (FET) acting as an electronic switch. The photodiodes are initially charged by connecting them to a known stable voltage by activating the FETs. Subsequently, the photodiodes are isolated by turning off the FETs. Upon exposure to X-rays, the scintillator produces light which discharges each photodiode in proportion to the X-ray exposure at the position of the diode. The diodes are then recharged by again connecting them to the known stable voltage. The charge used to restore the diode to its initial voltage is measured by a sensing circuit, and the value is digitized and stored.

In such a detector, the photodiodes and their associated FETs are typically organized in rows and columns. The gates of the FETs along a row are connected together, and the row electrodes are connected to scanning electronics. During read-out of the detector, rows of FETs are turned on sequentially, and an entire row of detector elements is read out at the same time. Because of imperfections in the FETs, a time-dependent background current is generated when the FETs are turned on and off. The result is an offset signal that is unrelated to X-ray exposure. The offset signal is typically referred to as switching charge retention. Since the rows are read sequentially, a portion of the switching charge retention is row correlated, i.e. the switching charge retention is roughly the same for all elements in a given row, but varies from row to row. But to make matters more complicated, the switching charge retention for a given row changes with the frame rate of the imaging system.

Also, there are other offset signals that are generated due to both the photosensitivity of the FETs and the capacitance between the photodiodes and the data lines. When light hits the array, the FETs tend to conduct and, much like in normal operation, exhibit charge retention at the conclusion of the X-Ray exposure. Furthermore, as the photodiodes discharge, the capacitance between the photodiode and the data line also experiences a change in charge. Due to the resistance of the data line, the effect may take some time to settle, looking like another source of signal while the effect decays. The composite offset signal, due to exposure, may be referred to as photoconductive charge retention.

The switching charge retention and composite photoconductive charge retention combine to create an offset signal in the elements of the array that should be accounted for during read-out. In the absence of the offsets, the converting circuitry would require only the dynamic range and resolution of signals generated by normal X-ray exposure. In practice, however, the dynamic range of the offset signals may be larger than the dynamic range of useful signals for imaging. For practical reasons, converting circuits have limitations in input signal dynamic range, conversion resolution, and conversion speed. In the absence of compensation for the offsets, the converting circuitry would be required to accommodate an increased input dynamic range without sacrificing resolution and speed.

Previous efforts to solve the problem of charge retention have only accounted for switching charge retention and relied on a prior calibration of the switching charge retention for a constant frame rate as in U.S. Pat. No. 5,604,347 to Petrick et al. Initially, a calibration is performed to measure the average offset of each row. Subsequently, an offset compensation value for each row is stored in the memory of a converting circuit. The stored compensation values are added to the incoming signals during operation of the detector. However, the method does not properly compensate for the contribution of photoconductive charge retention nor an imaging system where the frame rate is varying.

A need exists for an approach to reduce signal conversion times by adjusting for row-to-row variations caused by both switching charge retention as a function of frame rate and photoconductive charge retention as a function of X-Ray photon flux in order Summary of Invention to increase imaging frame rate.

Summary of Invention

SUMMARY OF INVENTION

Embodiments of the present invention provide an X-ray system for generating and displaying a plurality of image frames corresponding to internal structure within a subject such that signal conversion time is reduced, thus increasing frame rate. The diagnostic X-ray system comprises an X-ray tube for generating X-ray signals, a solid-state detector module responsive to the X-ray signals and an image processing module generating a plurality of normalized detector signals for a current image frame. The normalized detector offset signals for the current frame are dynamically adjusted for row-to-row variations in charge retention of a detector panel array of the solid-state detector module as frame rate changes, and as the X-Ray photon flux changes from frame to frame.

Apparatus is provided to reduce signal conversion time of an X-ray system in order to increase frame rate. The X-ray system includes a scintillator converting X-ray photons to light photons, an array of photodiode/field-effect-transistor pairs abutting the scintillator and being responsive to the light photons to affect discharge of the array, and read-out electronics to read a current row of the array. The read-out electronics are connected to columns of the array and are responsive to charge. The readout electronics are used to generate a set of normalized detector signals such that the set of normalized detector signals is adjusted for variations in signal strength caused by temporal row-to-row and frame-to-frame variations in charge retention in the array.

A method is also provided to minimize signal conversion time for a solid-state detector panel of an X-ray system in order to increase frame rate. A measurement of a set of induced signal offsets caused by time varying charge retention associated with the detector panel is performed during a phantom time segment prior to normal signal readout of the detector panel for a current image frame. A set of adjustment values is generated in response to the set of induced signal offsets. Subsets of signal values of the detector panel are detected and normalized to a predetermined signal dynamic range as part of normal signal readout of the detector panel in response to the set of adjustment values, thus generating a set of normalized detector signals.

Certain embodiments of the present invention afford an approach to generating and displaying a plurality of X-ray image frames at an increased frame rate by reducing the signal conversion time for a solid-state detector of an X-ray system.

BRIEF DESCRIPTION OF DRAWINGS

FIG. 4 is an exemplary illustration of indexing into a look-up-table to extract adjustment values in accordance with an embodiment of the present invention.

DETAILED DESCRIPTION

Figure 1:
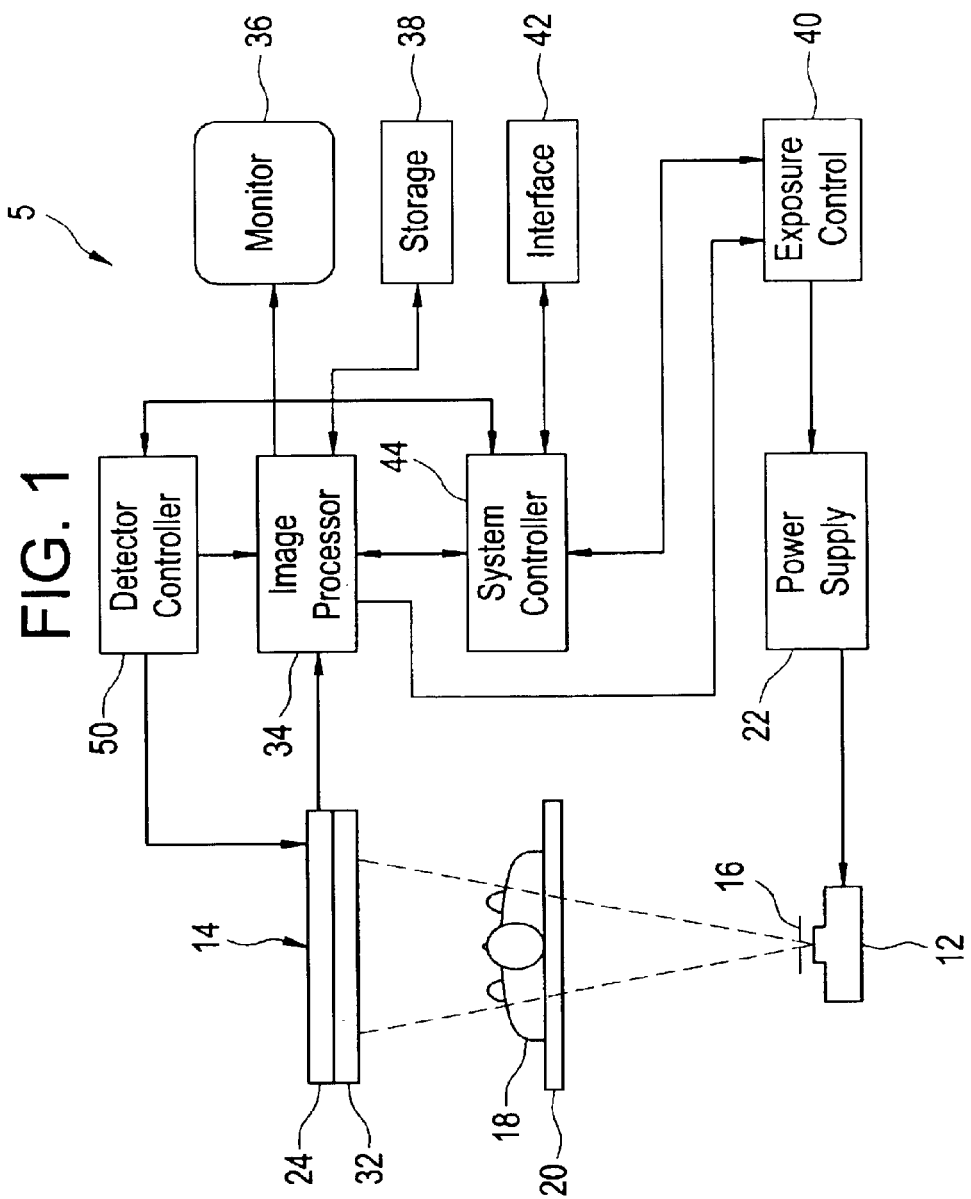
FIG. 1 is a schematic block diagram of a diagnostic X-ray system illustrating the various elements of the X-ray system in accordance with an embodiment of the present invention.

FIG. 1 is a schematic block diagram of the diagnostic X-ray system 5 showing the major elements of the X-ray system 5 in accordance with a preferred embodiment of the present invention. The X-ray system 5 comprises an X-ray tube 12, an X-ray detector module 14, and a collimator 16. X-rays are transmitted from the X-ray tube 12, via the collimator 16, to the X-ray detector module 14. An X-ray of a patient 18 is taken by placing the patient 18 between the collimator 16 and the X-ray detector module 14, placing X-ray transmissive material 20 on the side of the patient 18 facing the collimator 16, and exposing the patient 18 to X-rays for an amount of time. The X-ray system 5 further includes a power supply 22 for exciting the X-ray tube 12.

Figure 2:
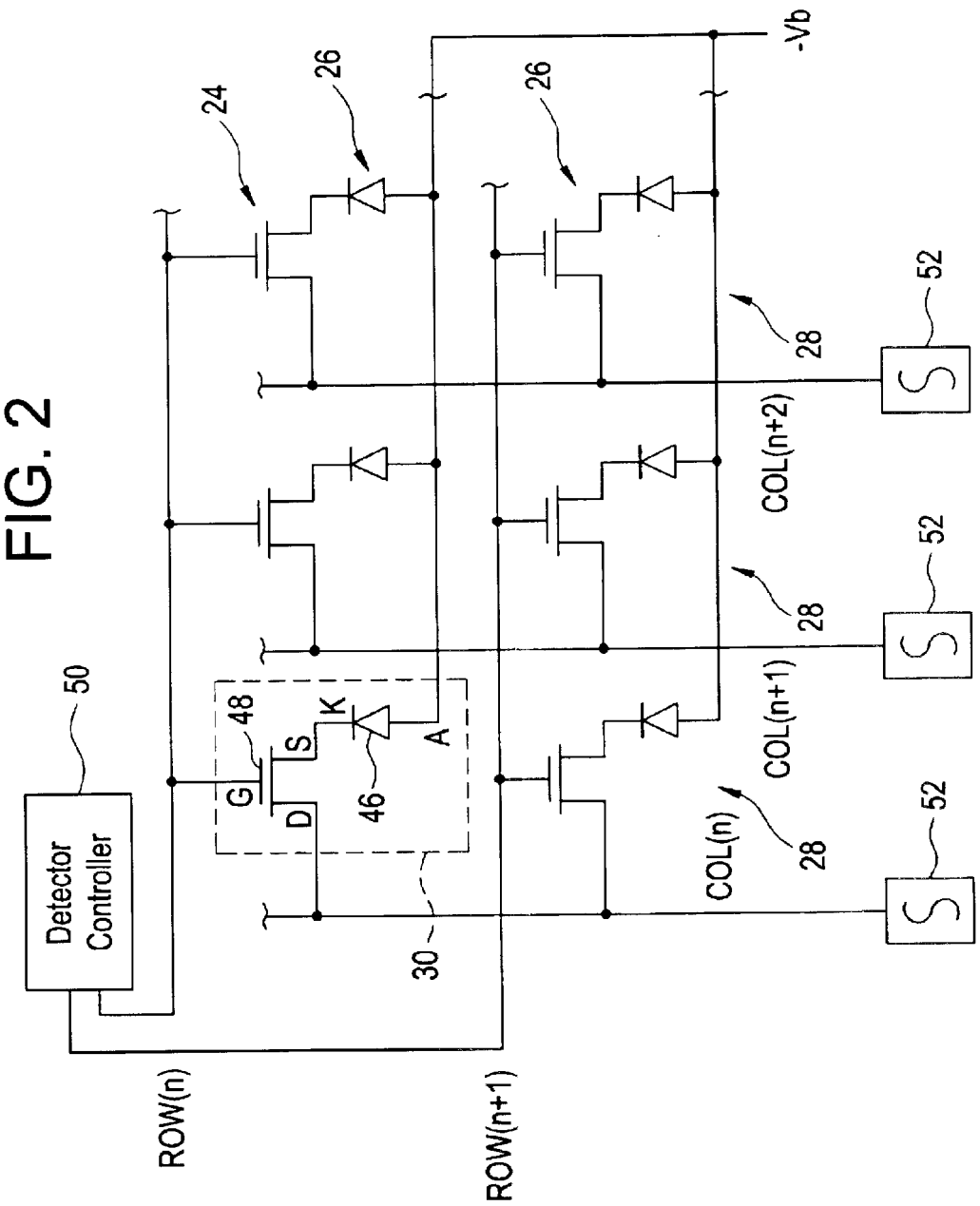
FIG. 2 illustrates elements of rows and columns of a detector array of the X-ray system of FIG. 1 in accordance with an embodiment of the present invention.

As shown in FIG. 2, the X-ray detector module 14 includes a detector array 24 of rows 26 and columns 28 of photo-detector elements 30. The detector module 14 further includes a scintillator 32 between the detector array 24 and the patient 18 such that the scintillator 32 is abutting the detector array 24 in order to convert X-rays to light.

The X-ray system S further includes an image processor 34 that receives the output from the array 24 and processes the image received by the array 24. The X-ray system 5 further includes a monitor 36 connected to the image processor 34, for displaying the processed image, and includes an image storage device 38 for archiving the processed image if desired. The X-ray system 5 further includes an exposure control circuit 40 that receives a brightness signal from the image processor 34 and regulates the power supply 22 to regulate X-ray exposure.

The X-ray system 5 further includes an operator interface 42 and a system controller 44 that controls the operation of the rest of the X-ray system 5 and receives commands from a human operator via the operator interface 42.

The detector array 24 is made of layers of thin film material including one or more layers of amorphous silicon. As shown in FIG. 2, each photo-detector element 30 of the detector array 24 comprises a photodiode 46 that converts photons to an electrical signal. Each photodiode 46 has an anode A and a cathode K, and is a large area photodiode taking up most of the area in each element 30 so as to intercept a large fraction of the light that hits the element 30. Each element 30 further includes a thin film transistor 48. In the illustrated embodiment, each transistor 48 is a field-effect-transistor (FET) having a gate G, a drain D, and a source S.

The cathode K of the photodiode 46 in each element 30 is connected to the source of the transistor in the element. The anodes A of all the photodiodes 46 in the detector array 24 are connected together and to a negative bias voltage $V_b$. The drains D of transistors in respective columns are connected to respective column electrodes COL(n), COL(n+1), COL(n+2) . . . , and the gates of transistors in respective rows are connected to respective row electrodes ROW(n), ROW(n+1) . . . The X-ray system 5 further includes a detector controller 50 connected to the system controller 44 and to the row electrodes. The column electrodes are connected to the image processor 34.

To acquire an image from the detector array 24, the detector controller 50 connects the column electrodes to a known, stable voltage $V_c$ provided by the read-out electronics that, for example, may be within two volts of ground. While the column electrodes are connected to the voltage $V_c$, the detector controller 50 connects the row electrodes to a voltage $V_{on}$ which is positive relative to $V_c$. As a result, the photodiodes are back biased. The transistors conduct and a charge is placed on each of the capacitances associated with the photodiodes. Once the photodiodes have been charged, the detector controller 50 connects the row electrodes to a voltage $V_{off}$ which is negative relative to both $V_c$ and $V_b$ to turn the transistors off and prevent them from conducting. The array is then exposed to light energy, such as produced by the scintillator 32 being exposed to X-rays. The photodiodes conduct and the capacitance associated with each photodiode is partially discharged. The amount of charge removed from the capacitance associated with each photodiode depends on the intensity and duration of the light energy striking that particular photodiode. Because the duration of exposure to light energy is the same for each of the photodiodes, the amount of charge removed from the capacitance associated with the photodiodes represents the intensity of the light energy striking the various photodiodes, and is read by measuring the amount of charge required to recharge each photodiode's capacitance. The variation in charge removed from different photodiodes constitutes an image of the light striking the detector.

The amount of charge removed from the capacitance associated with each photodiode is measured by instructing the detector controller 50 to connect the rows, one at a time, to the voltage $V_{on}$ and respectively measure the charge required, at the column electrode for each diode in the row, to recharge the diodes' capacitance to the same voltage prior to exposure to the light energy. Image processor module 34 includes a sensing circuit, including an integrator 52 in a preferred embodiment, connected to each column of the array 24. The integrator 52 is preferably a low noise integrator without offset or input bias currents. The detector controller 50 returns each row to $-V_{off}$, and the sensing circuits are all cleared (i.e. integrators are reset) after a row is read so as to prepare the sensing circuits for reading the next row.

Because the output signal from the detector array 24 is very small, circuitry for measuring charge removed from the photodiodes is very sensitive. The transistors 48 in the array 24 exhibit "switching charge retention" where not all signal leaves the amorphous silicon transistors of the array when a row is returned to $-V_{\mathit{off}}$, but rather bleeds out slowly over time. The charge retained by the transistors in a row being read has the effect of an offset for elements being read in the row. The offset may be quite large compared to the dynamic range of the output signals desired to be measured. The switching charge retention also changes with imaging frame rate.

Also, charge may be retained by the FET when the FET is activated by exposure to the light energy. The charge retained is called "photoconductive charge retention" and also has the effect of an offset. The total charge retention is the composite of the switching charge retention and the photoconductive charge retention and yields a composite offset. The composite offset would require that the dynamic range of the sensing circuitry be very large if not compensated for in some manner. A large dynamic range means having many detection levels in order to discern signal gray levels with a desired amount of resolution. Each detection level takes a certain amount of time $T_{detect}$. If many detection levels are required to be checked for a given row during the detection process, then the result may be a decrease in imaging frame rate. Since $T_{detect}$ is typically constant for a given detector array module, it is desirable to reduce the number of detection levels that are checked in order to increase the frame rate without losing signal resolution. The number of detection levels to be checked may be reduced by adjusting for the offset due to total charge retention on a row-by-row basis.

In U.S. Pat. No. 5,604,347 to Petrick et al., a solid-state X-ray detector makes use of row variable offsets in order to reduce the linear range of signal conversion, thereby reducing the time required for signal conversion and increasing the effective frame rate. When the time between frames is fixed, the offset induced by switching charge retention may be characterized as part of the development process and removed during the operation of the X-ray system by providing a row variable offset profile that is based on the characterization. The result is a signal conversion ramp that has a linear portion that has been reduced. The linear portion of the signal conversion ramp is used to measure the offset of a "dark image" (no X-ray exposure) that is then subtracted from an image containing X-ray signal information, thus removing the offset. The solution of U.S. Pat. No. 5,604,347 works well for fixed frame rates, where the time between frames is constant, meaning that the decay of the charge retention induced offset is also constant from frame to frame.

An additional challenge is presented, however, when it is desired to make the time between frames variable. At one extreme, there would be no need for row variable offset compensation when the time between frames is zero, since the charge retention contribution is constant (the decay of early rows may be exactly replaced with the most recently activated row being read out). The linear portion of the conversion ramp may simply have to cover the range of offsets expected from an individual pixel or element of the detector array 24 (for example, photodiode leakage), rather than the additional range required due to charge retention. At the other extreme, the charge retention builds from its most negative value (infinite time between frames, meaning that there is no contribution from prior rows for the first row), to a steady state value (where the charge retention offset contribution becomes constant), and the range of offsets required becomes a maximum. It is at the second extreme that row variable offset compensation provides the most benefit. Furthermore, even with relatively little time between frames, the offset dispersion may be adversely affected as signal gain is increased. As signal gain increases, the linear range dedicated to the conversion of offset also increases, adversely affecting the time that signal conversion takes.

In embodiments of the present invention, the offset due to total charge retention is compensated for by, first, performing phantom measurements of the detector array 24 for a current image frame to be read out prior to normal signal read-out of the detector array 24. Then, the phantom measurements may be used to generate adjustment values that may be applied during subsequent normal signal read-out to correct for the offsets caused by the total charge retention. As result, the adjustment values are dynamically updated for each image frame, compensating for changes in charge retention due to changes in both imaging frame rate and photoconductive charge retention, and having the effect of increasing overall imaging frame rate. The phantom measurements are done once before the read-out of each image frame, not for each row to be read.

Figure 3:
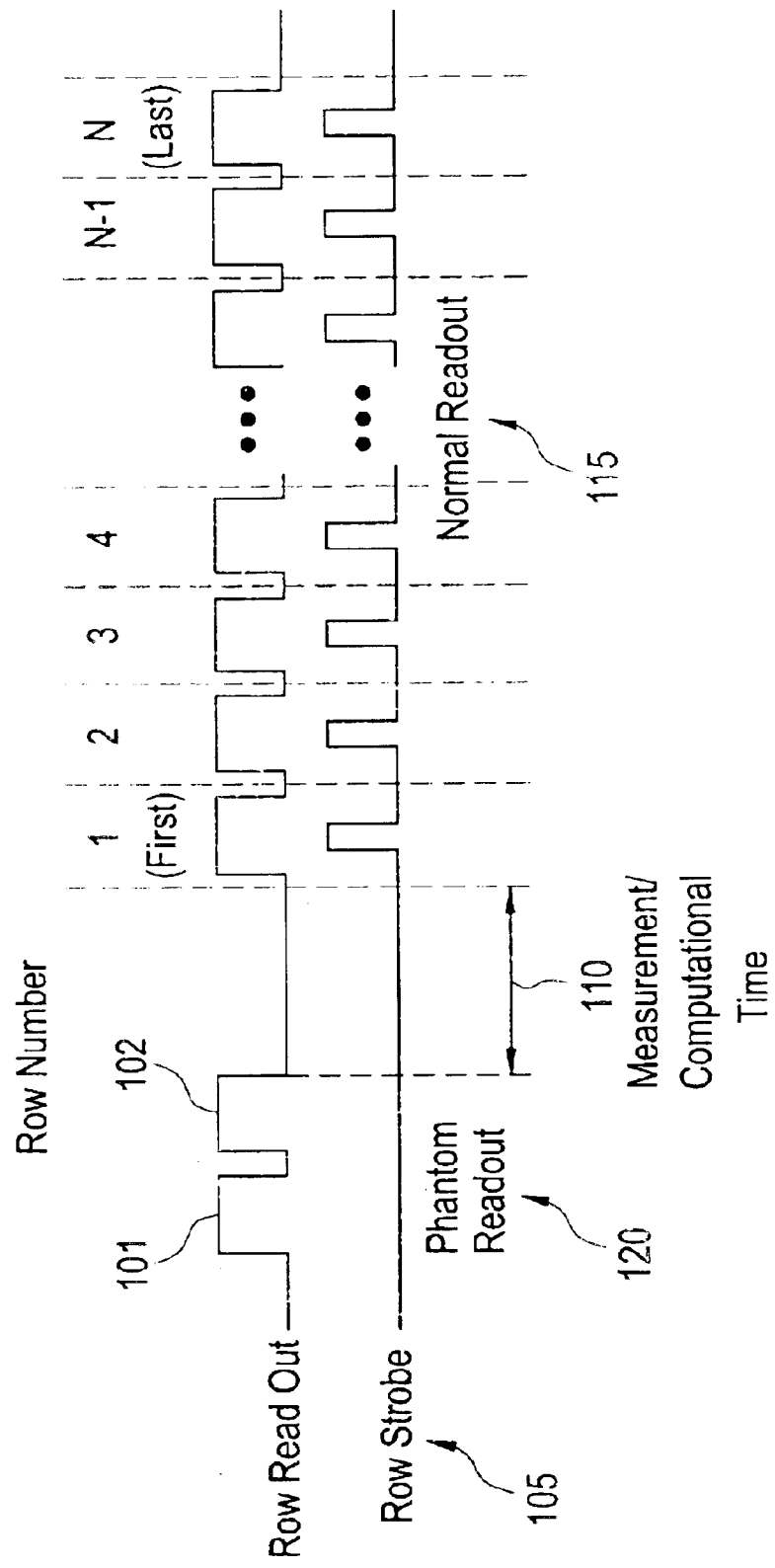
FIG. 3 illustrates the timing associated with taking phantom measurements of the detector array of FIG. 2 and reading out the detector array in accordance with an embodiment of the present invention.

FIG. 3 illustrates the process of performing phantom measurements on the detector array 24 and then reading out the rows of the detector array 24. In FIG. 3, two phantom measurements, 101 and 102, are made prior to normal read-out 115 of the detector array 24 during phantom read-out 120. When a detector row is normally read out, a row strobe 105 is applied to the gates of the transistors in that row for a certain period of time. The amplitude of the row strobe is $V_{on}$ as previously described. Each element of the row is read out at the same time by the read-out electronics in the image processor 34 along columns of the detector array 24 as previously described. However, when the phantom measurements (101 and 102) are made, the row strobe signals are turned off. As a result, the measurements represent the initial charge retention associated with the current imaging frame. If two phantom measurements are taken, as shown in FIG. 3, the two measurements may be averaged to yield a composite phantom measurement. More than two phantom measurements may be taken, if desired, to obtain a more accurate representation of the charge retention.

Adjustment values are then generated during a measurement/computational time segment 110 in response to the phantom measurements. Once the adjustment values are generated, they may be applied during the process of normal readout 115 so as to compensate for the offsets caused by the total charge retention for each row, thus reducing the number of detection levels that are required for normal signal detection. Each row, or scan line, is effectively being normalized with respect to the other rows in the current frame for both the X-Ray image and the dark frame used for individual pixel offset measurements before subsequently doing a dark frame subtraction after conversion. As a result, the input dynamic range of the read-out electronics does not need to be very large and signal detection and conversion may take place in a shorter time period, thus increasing overall imaging frame rates.

The phantom measurements may be used to compute the adjustment values or they may be used to index into a look-up-table (LUT), as shown in FIG. 4, where the adjustment values are stored in memory of the read-out electronics. Considering that charge retention usually builds to a steady state, generating the adjustment values may be as simple as indexing into the LUT where charge retention is characterized in the LUT with an infinite time between image frames. The index determines the location in the LUT for the adjustment value of the first row of the detector array. Subsequent adjustment values for subsequent rows come from subsequent LUT entries.

More sophisticated indexing techniques may be made using the LUT to properly compensate for the photoconductive charge retention component of the total charge retention. The adjustment values, whether computed on the fly for each image frame or extracted from a LUT, are a function of the measured charge retention, the expected signal dynamic range, and other electronic offsets. In the X-ray system, the thickness of the Cesium Iodide is controlled and the expected signal dynamic range is controlled based on control of transmitted X-ray intensity. Therefore, the expected magnitude of the photoconductive charge retention may be characterized and therefore anticipated.

FIG. 4 illustrates one embodiment of the LUT as the LUT would be applied to four different times between frames (infinite time, X time, Y time, and zero time, in descending order). The LUT in the bottom half of FIG. 4 shows how one LUT, characterized by infinite time between frames, may be used to provide the same adjustment profiles. The adjustment profile is simply started at different places in the LUT, depending upon the phantom measurements, which are greatly influenced by the time between imaging frames. Only L values are shown, where L<N and N is the total number of rows, due to the fact that a steady state value is reached when the charge retention contribution decays at the same rate that additional rows are read out. When the last value in the LUT is reached, that value is simply repeated for all the remaining rows to be read out.

In a first embodiment of the present invention, the adjustment values are applied during an acquisition time period 125 of normal readout 115. If a precise offset is induced, due to charge retention, on a signal that is expected to be outside the dynamic range provided by the read-out electronics, the total (signal plus offset) may be made to fall within the dynamic range provided by the read-out electronics without suffering an increase in conversion time. Conversion time is the time required to convert an integrated signal from an analog voltage to a digital value. In an embodiment of the present invention, a single conversion level comprises a time segment $T_{detect}$ of 64 nano-seconds.

Figure 5:
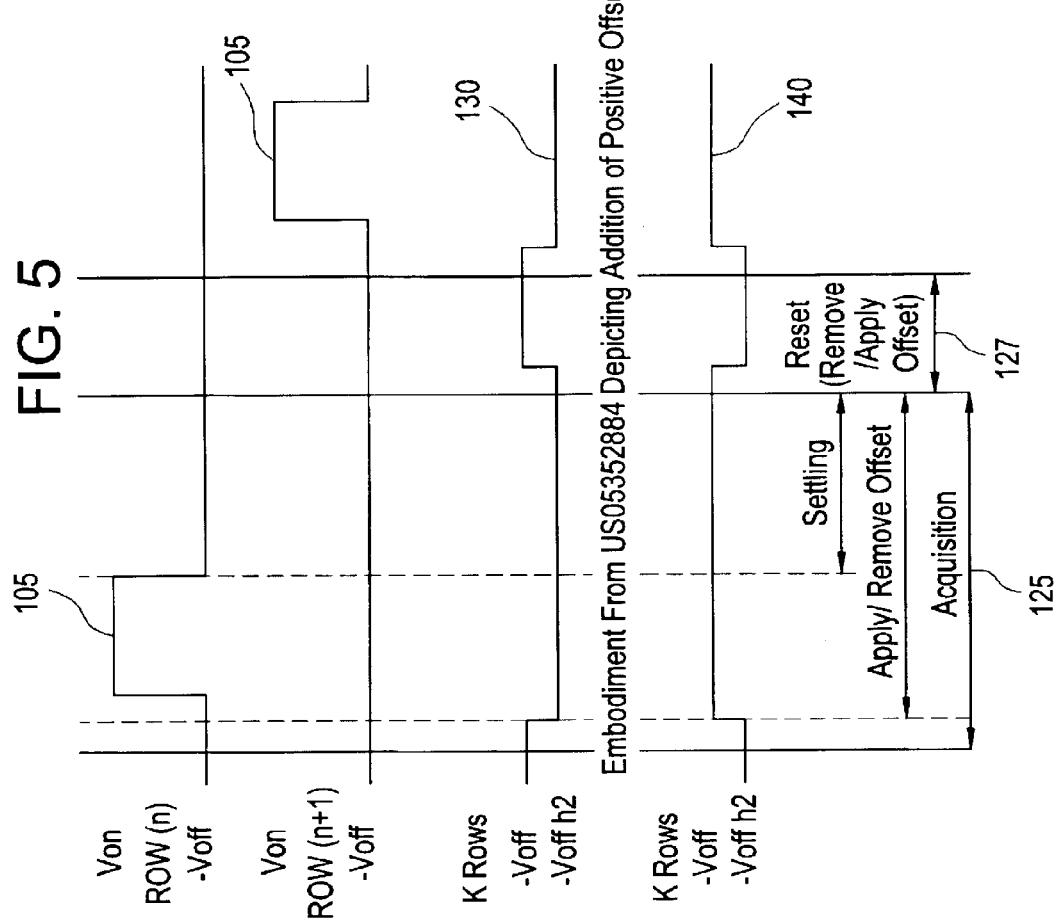
FIG. 5 illustrates the timing associated with applying adjustment signals to the gates of transistors corresponding to K rows of a detector array panel of the X-ray system of FIG. 1 in accordance with an embodiment of the present invention.

In order to achieve a compensating negative or positive offset, depending on what is required for a given row of the detector array 24, a number of rows may be used to provide the offset with the timing shown in FIG. 5. In a first case 130 a more negative voltage $-V_{offh2}$ is applied, to the gates G of j rows providing offset (where j is greater than or equal to one), during signal acquisition 125 of a given row to be read (e.g. ROW(n)) and is removed during reset 127 of the read-out electronics as shown in the timing diagram. The case 130 provides a positive offset to counter the effects of a negative charge retention induced offset. The counter case is shown in the timing diagram for the case 140 where a more negative voltage $-V_{offh2}$ is applied, to the gates G of j rows providing offset, during reset 127 of the read-out electronics for a given row to be read (e.g. ROW(n)) and is removed during signal acquisition 125, thus providing a negative offset to counter the effects of a positive charge retention induced offset.

The read-out electronics are bi-polar, allowing for the proper compensation of both positive and negative induced offsets. The number of rows may be changed and/or the difference between $-V_{off}$ and $-V_{offh2}$ many be changed to effectively achieve the same amount of compensation due to charge retention. Also, a similar effect may be induced if the voltage applied to induce the offset is more positive than $V_{off}$. As a result, $-V_{offh2}$ becomes $-V_{off}$ and $-V_{off}$ becomes $-V_{offi2}$, where $-V_{offh2} < -V_{off} < -V_{off\ offi2}$.

Alternatively, before $-V_{offh2}$ is applied, a signal gain of the read-out electronics (e.g. the gain of the integrators 52) may be adjusted first to help put the resultant integrated signal in a more appropriate dynamic range region. Then, when $-V_{offh2}$ is applied as described above, the resultant integrated signal value is in the pre-determined signal dynamic range of the conversion process, reducing the number of conversion levels needed for signal conversion and thus reducing the overall signal conversion time. The result has the desired effect of retaining a more compressed dynamic range for the read-out electronics (shorter time, higher frame rate) while effectively covering a larger dynamic range that is beyond that offered by the conversion process used.

The gain adjustment value and the offset value $-V_{offh2}$ are the computed adjustment values and/or adjustment values extracted from a LUT as previously described. More than one LUT may be implemented if desired (e.g. a first LUT for the gain adjustment value and a second LUT for $-V_{offh2}$). The computed and/or LUT adjustment values effectively compress the input signal dynamic range by a predetermined amount.

In a second embodiment of the present invention, the adjustment values are applied during a conversion time period 150 (see FIG. 7) during normal readout. Here, instead of applying adjustment values to certain rows during acquisition, adjustment values are applied during signal conversion 150 to effectively offset a signal conversion ramp 160 to the appropriate signal dynamic range.

Figure 6:
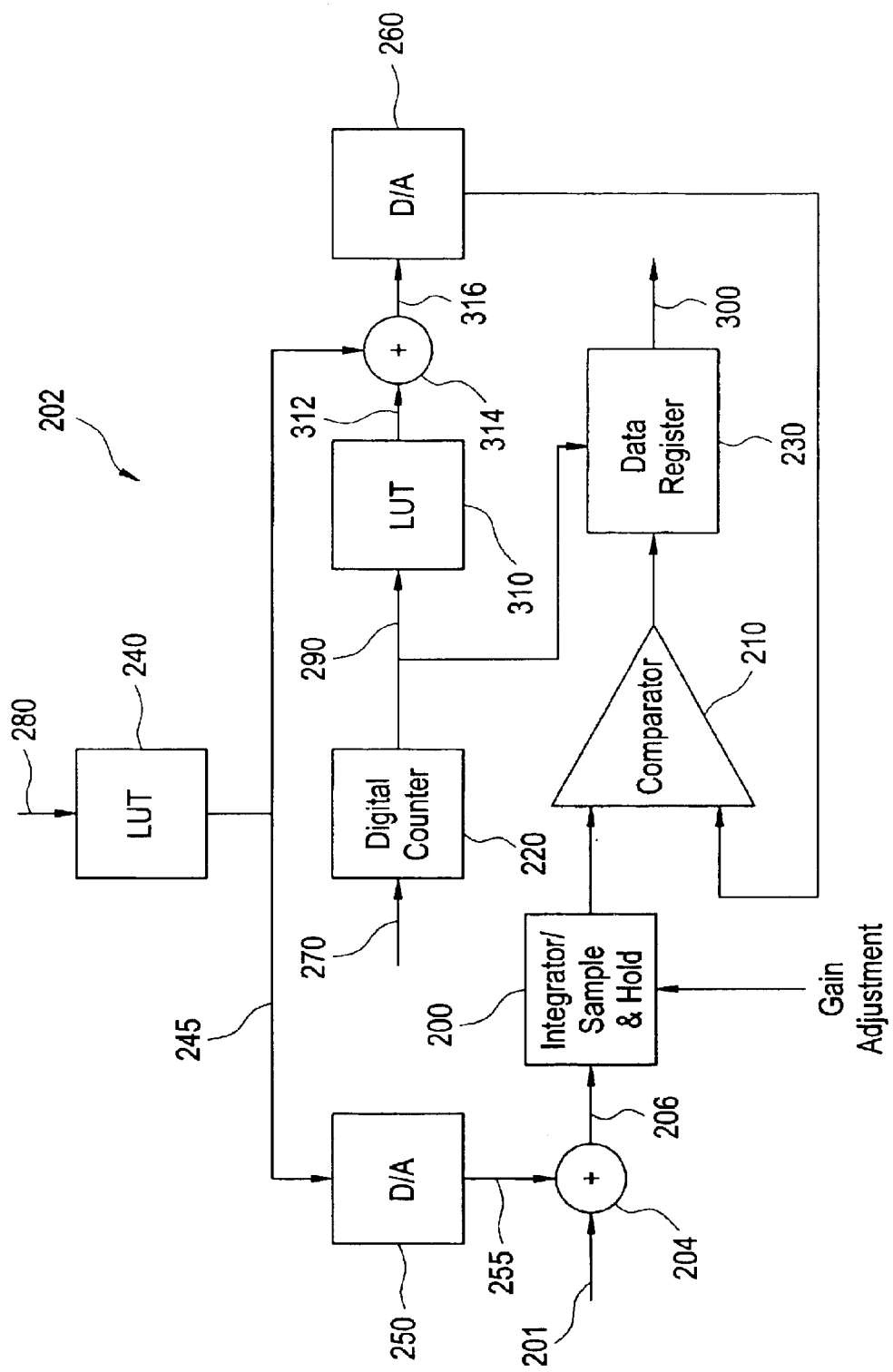
FIG. 6 is a schematic block diagram illustrating the read-out electronics of the X-ray system of FIG. 1 in accordance with an embodiment of the present invention.

FIG. 6 illustrates one embodiment of the read-out electronics of the present invention that performs both integration and signal conversion. The read-out electronics comprises an integrator/sample-and-hold circuit 200, an analog summation circuit 204, a comparator 210, a data register 230, a digital counter 220, a LUT 240, a second LUT 310, a digital summation circuit 314, a first digital-to-analog converter (D/A) 250 and a second D/A 260. During the signal integration time 125 for a given row being read out, the integrator/sample-and-hold circuitry integrates up the signal at input 206 (for each element in the row) corresponding to the amount of signal discharged during the X-ray exposure for the current frame for the pixel being read at input 201 in addition to an analog voltage generated by D/A 250 and added in an analog fashion by adder 204. D/A output 255 is controlled by the output 245 of LUT 240. The output of the integrator/sample-and-hold circuitry goes to a first input of the comparator 210. An output of D/A 260 goes to a second input of the comparator 210.

Figure 7:
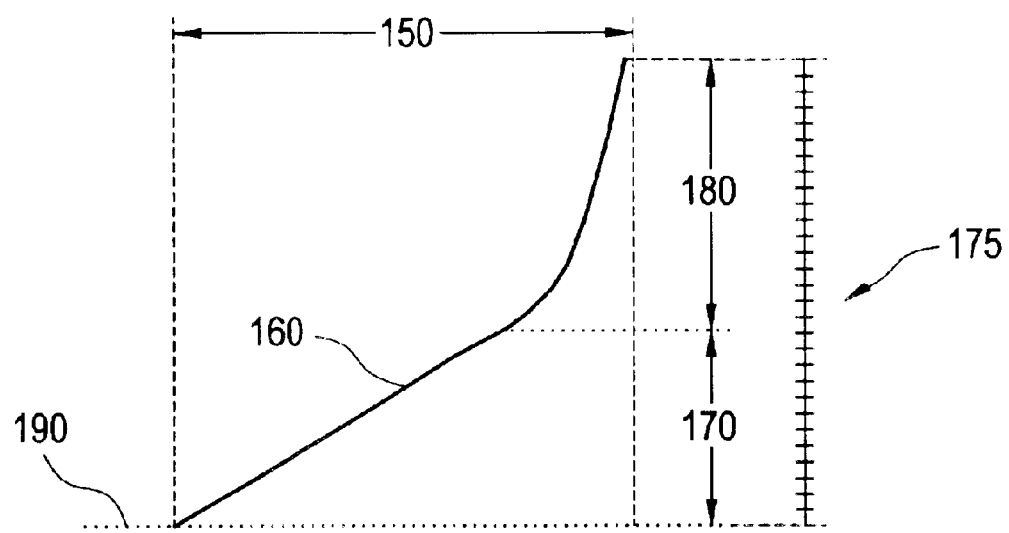
FIG. 7 illustrates a signal conversion ramp generated by the read-out electronics of FIG. 6 in accordance with an embodiment of the present invention.

When the value of the second input to comparator 210 is greater than or equal to the first input of comparator 210, a latch signal is output from comparator 210. The latch signal is an input to a data register 230 and latches a data value output from a digital counter 220. During signal conversion, the digital counter 220 starts counting and outputting a signal conversion ramp in response to a clock signal 270 where the signal conversion ramp has a pre-determined, fixed number of discrete levels n 175 defining a fixed dynamic range as shown in FIG. 7. The signal conversion ramp comprises a linear region 170, a quadratic region 180, and a row variable offset level 190 the digital values for which are contained in LUT 310.

In the prior art, LUT 240 would contain only the digital values for the expected range of switching charge retention offsets for a fixed frame rate and time between frames. Input 280 in the prior art would have simply been a row address. LUT 240 effectively adds the expected (from prior characterization at fixed frame rates) charge retention offset. As shown by the diagram, the offset may be added in an analog fashion, by summation circuit 204 during signal acquisition (first embodiment), or in a digital fashion, by summation circuit 314 during conversion (second embodiment), or a combination of both, perhaps with more than one LUT 240 to feed each of the summation circuits independently.

In the prior art, input 280 to LUT 240 would have simply been a digital representation of the row presently being read (i.e. a row "address"), and would have been a fixed value for a given row from frame to frame. In an embodiment of the present invention, LUT 240 contains many more values, accounting for characterization of charge retention offsets with time between frames varying from zero time to that time at which the charge retention decays to a value close enough to zero to be of no concern. In an embodiment of the present invention, input 280 to LUT 240 would be variable for a given row from frame to frame dependent upon the signal measured during the "phantom rows".

The first embodiment adds the offsets in an analog fashion during signal acquisition, using summation circuit 204. The second embodiment adds the offsets during conversion using summation circuit 314. Note that a third D/A and an analog summation performed after D/A 260 could be substituted for the digital summation circuit 314 in order to achieve the same effect.

The linear region 170 of the signal conversion ramp 160 defines the dynamic range of the expected "dark frame" values, when no signals due to X-ray exposure are present in the detector array. Therefore, if adjustment for charge retention is done correctly, all converted integrated signals 300 out of the read-out electronics should end up in the linear region 170 of the signal conversion ramp 160 when no X-ray exposure has been made. The linear region 170 is also significantly smaller than it would need to be if adjustment for charge retention was not being performed.

The quadratic region 180 is where expected values of X-ray signals may fall. The region is quadratic since X-ray quantum noise is proportional to the square root of X-ray intensity. Therefore, as X-ray intensity increases, it makes sense to increase the ramp values in a quadratic manner, making larger jumps in ramp levels, so as not to waste time trying to detect X-ray signals with a greater number of smaller, linear steps. The signal conversion ramp 160 is fixed for all signals to be detected in the detector array except that the row variable offset level 190 gets adjusted based on the phantom measurements previously described based on the characterization of the detector array panel with respect to charge retention. Again, the linear region 170 is significantly smaller than it would need to be if adjustment for charge retention was not being performed.

In a "light image" (X-ray exposure has occurred), high X-ray penetrations should end up in the higher region of the quadratic portion of the signal conversion ramp, lower X-ray penetrations should end up in the lower region of the quadratic portion of the signal conversion ramp, and no X-ray penetrations should end up in the linear region of the signal conversion ramp.

In either embodiment of the present invention, the adjustment values may be generated from the phantom measurements by indexing into the LUT 240 at LUT addressing input 280. For a given row j, the LUT outputs a signal offset value at input 245 to D/A 250 and/or an offset level value to digital summation circuit 314. The offset level value at input 245 corresponds to the row variable offset 190 shown in FIG. 7. The adjustment values effectively match the dynamic range of the signal conversion ramp contained in LUT 310 to the expected signal range out of the integrator/sample-and-hold circuit 200.

D/A 260 converts the level out of LUT 310, for a given clock cycle, added to that of LUT 240, for a given row, to an analog ramp value. The analog ramp value is input to comparator 210 along with the signal out of integrator/sample-and-hold 200 corresponding to an element of the row j currently being read. The comparator 210 outputs a latch signal when the analog ramp value equals or exceeds the integrated signal level. Since the output of digital counter 220 also goes to data register 230, the digital ramp value corresponding to the analog ramp value is latched in data register 230 when the latch signal is output from the comparator 210. The latched value in the data register represents the adjusted or row-normalized value of the integrated signal for one element of the row j being read out, adjusting for the total charge retention induced offset for the row j. Not shown is a LUT fed by data register 230 that expands the compressed digital values (the counter only counts by "1" for each clock cycle) to that covered by D/A 260.

In the first embodiment of the present invention, there is an analog summation circuit 204, an integrator/sample-and-hold 200, a comparator 210, and a data register 300 for each column of the detector array, since each element of a row is read out at the same time and since only one row is read out at a time. There is only one D/A 250, one D/A 260, one digital counter 220, and one LUT 240 in the embodiment since the same signal conversion ramp 160 is used to read out each row. There is no digital summation circuit 314. The embodiment may be used to contain the dynamic range of the expected input signal 201 to that which may be acquired by integrator/sample-and-hold 200 without that circuit reaching saturation, by virtue of the analog summation prior to signal acquisition, an advantage that the first embodiment has over the second. The second embodiment employs no analog summation circuit 204 or D/A 250, but does include one digital summation circuit 314.

The LUT 240 is configured, based on a prior characterization of charge retention versus frame rate as previously described, to allow the dynamic range of the signal conversion ramp 160 to be matched to the expected dynamic range of the integrated signals. As a result, total charge retention is adjusted resulting in a fixed number of conversion levels n 175 that may be used for detection of all signals from the detector module, and resulting in reduced signal conversion times and increased frame rates.

Again, as an alternative for the second embodiment, the adjustment values may be computed instead of pulled out of a LUT. Also, there may be a first LUT for the analog adjustment values and a second LUT for the digital adjustment values.

In summary, a first embodiment of the present invention applies adjustment values to the gates of rows of FETs not currently being read out representing an analog summation input of the signal integrators by virtue of the parasitic capacitance between every row and every column of the detector, during an acquisition time of the row being read out, to adjust for charge retention for a given image frame. A second embodiment of the present invention applies adjustment values to a signal conversion ramp to match the dynamic range of the signal conversion ramp to the expected dynamic range of the integrated signals for a row being read out, effectively defining a pre-determined signal dynamic range.

As an alternative, both embodiments described above may be combined, applying adjustment offset values to certain rows during acquisition to compensate for a part of the charge retention induced offsets and applying other adjustment values to the signal conversion ramp during conversion to compensate for another part of the charge retention induced offsets.

An advantage of the above embodiments is that the adjustment values are applied dynamically in real time in a controlled and measured manner (using the phantom measurements as feedback to the read-out electronics), reducing the required dynamic range rather than simply negating an undesirable effect of an expected charge retention induced offset.

Another advantage of the above embodiments is that they do not suffer from the one frame lag in adjustment that typical automatic brightness and/or gain algorithms typically induce. If the charge retention offset were measured using the image data from the preceding image frame, the adjustments would not take effect until the frame following the measurement, at the earliest.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiments disclosed, but that the invention will include all embodiments falling within the scope of the appended claims.

What is claimed is:

1. In a diagnostic x-ray system generating a plurality of image frames at varying frame rates, a method to minimize signal conversion time for a solid-state detector panel of said x-ray system, said method comprising:

measuring a set of induced signal offsets, whether positive or negative, caused by time varying charge retention associated with said detector panel during a phantom time segment prior to normal signal readout of said detector panel for a current image frame;

generating a set of adjustment values in response to said set of induced signal offsets; and reading out subsets of signal values of said detector panel to a pre-determined signal dynamic range as part of said normal signal readout of said detector panel in response to said set of adjustment values, thus generating a set of normalized detector signals.

2. The method of claim 1 wherein said generating said set of adjustment values comprises indexing into at least one look-up-table (LUT) and reading said adjustment values from said at least one LUT prior to said normal signal readout of said detector panel for said current image frame, said at least one LUT being previously generated based on, at least in part, a prior characterization of panel charge retention as a function of said subsets and frame rate.

3. The method of claim 1 wherein said generating of said set of adjustment values comprises computing said set of adjustment values prior to said normal signal readout of said detector panel for said current image frame, said computing being based on, at least in part, a prior characterization of panel charge retention as a function of said subsets and frame rate.

4. The method of claim 1 wherein said reading out comprises adjusting a signal gain value and/or shifting a starting value of a signal conversion ramp, for each subset of said subsets of signal values based on said adjustment values, during a signal conversion time segment of said normal signal readout such that each of said set of normalized detector signals falls within said pre-determined signal dynamic range for said current image frame.

5. The method of claim 1 wherein said reading out comprises adjusting at least one signal gain and/or offset value corresponding to a first subset of photodiode/transistor pairs of said detector panel, wherein said first subset is currently being read out during a signal acquisition time segment of said normal signal read-out and corresponds to a subset of said subsets of signal values, and applying at least one adjustment value to a second subset of photodiode/transistor pairs of said detector panel, wherein said second subset is not currently being read out, such that each of said set of normalized detector signals corresponding to said first subset falls within said predetermined signal dynamic range for said current image frame.

6. The method of claim 1 wherein any subset of said subsets of signal values of said detector panel corresponds to charges built up on at least one row of photodiode/transistor pairs of said detector panel.

7. The method of claim 1 wherein said charge retention comprises switching charge retention caused by switching field-effect-transistors on and off in said detector panel.

8. The method of claim 1 wherein said charge retention comprises photoconductive charge retention caused by photon signals impinging upon photodiodes in said detector panel.

9. The method of claim 1 wherein said charge retention comprises both switching charge retention caused by switching field-effect-transistors on and off in said detector panel and photo-conductive charge retention caused by photon signals impinging upon photodiode/transistor pairs in said detector panel.

10. In a diagnostic X-ray system generating a plurality of image frames at varying frame rates, apparatus to minimize signal conversion time of said X-ray system, said apparatus comprising:

a scintillator converting X-ray signals to photon signals;

an array of photodiode/field-effect-transistor pairs abutting said scintillator and being responsive to said photon signals to affect charge build-up in said array; and read-out electronics to read a current row of said array to be read, said readout electronics being connected to columns of said array and being responsive to said charge build-up to generate a set of normalized detector signals in response to phantom measurements such that said set of normalized detector signals is adjusted for offsets in signal strength, whether positive or negative, caused by temporal tow-to-row variations in charge retention in said array.

11. The apparatus of claim 10 wherein said read-out electronics comprises:

a set of signal integrator/sample-and-hold circuits responsive to a signal value and changes in said charge build-up along columns of said array to generate a corresponding set of integrated signals being proportional to said changes in charge build-up for each of said photodiode/field-effect-transistor pairs in said current row being read out; a digital counter responsive to a clock signal and a row variable offset value to generate an offset signal conversion ramp for said current row being read out and wherein said offset signal conversion ramp is derived from a single, pre-determined signal conversion ramp that is common for all rows to be read out;

a corresponding set of comparators responsive to said corresponding set of integrated signals and to said offset signal conversion ramp to generate a corresponding set of latch signals when said corresponding set of integrated signals is equal to or greater than a current level of said offset signal conversion ramp for said cw-rent row being read out; and a corresponding set of data registers responsive to said offset signal conversion ramp and said corresponding set of latch signals to capture said set of normalized detector signals in said corresponding set of data registers for said current row being read out.

12. The apparatus of claim 11 further comprising a first digital-to-analog converter responsive to a digitized version of said offset signal conversion ramp to generate an analog version of said offset signal conversion ramp for said current row being read out.

13. The apparatus of claim 11 further comprising a second digital-to-analog converter responsive to a digital version of said signal value to generate an analog version of said signal value for said current row being read out.

14. The apparatus of claim 11 wherein said row variable offset value offsets said pre-determined signal conversion ramp such that said corresponding set of integrated signals falls within the dynamic range of said offset signal conversion ramp for said current row being read out.

15. The apparatus of claim 11 further comprising at least one look-up-table (LUT) storing in a memory a single, predetermined set of row variable offset values wherein said row variable offset value for said current row being read out is generated by indexing into said at least one LUT based on taking at least one phantom measurement of said array prior to normal signal readout of said array.

16. The apparatus of claim 10 wherein at least one row variable offset value is computed for said current row to be read out based on taking at least one phantom measurement of said array prior to normal signal readout of said array.

17. The apparatus of claim 10 wherein at least one row variable offset value is applied to field-effect-transistors of at least one row of said array during an acquisition time segment of said current row being read out during normal signal readout, said at least one row being a different row than said current row being read out.

18. The apparatus of claim 10 wherein said charge retention comprises switching charge retention due to field-effect-transistors in said array switching on and off.

19. The apparatus of claim 10 wherein said charge retention comprises photoconductive charge retention caused by said photon signals.

20. The apparatus of claim 10 wherein said charge retention comprises both switching charge retention due to field effect-transistors in said array switching on and off and photo-conductive charge retention caused by said photon signals.

21. A diagnostic X-ray system for generating and displaying a plurality of image frames corresponding to internal structure of a subject, said diagnostic X-ray system comprising:

an X-ray tube for generating X-ray signals;

a solid-state detector module responsive to said X-ray signals and generating a plurality of charges representative of charge retention in response to phantom measurements and X-ray intensity; and an image processing module responsive to said plurality of charges and generating a plurality of normalized detector signals for a current image frame, said normalized detector signals being dynamically adjusted for variations in charge retention, whether positive or negative, as frame rate changes.

22. The diagnostic X-ray system of claim 21 further comprising a collimator to direct said X-ray signals towards said solid-state detector module.

23. The diagnostic X-ray system of claim 21 further comprising a detector controller module interfacing to said image processing module and said solid-state detector module to provide control signals to said image processing module and said solid-state detector module.

24. The diagnostic X-ray system of claim 21 further comprising a system controller interfacing to said image processing module and a detector controller module to provide system control signals to said image processing module and said detector controller module.

25. The diagnostic X-ray system of claim 21 further comprising a monitor interfacing to said image processing module for displaying said normalized detector signals to a user of said system.

26. The diagnostic X-ray system of claim 21 wherein said charge retention comprises switching charge retention caused by switching field-effect-transistors on and off in said detector panel.

27. The diagnostic X-ray system of claim 21 wherein said charge retention comprises photo-conductive charge retention caused by photon signals impinging upon photodiodes in said detector panel.

28. The diagnostic X-ray system of claim 21 wherein said charge retention comprises both switching charge retention caused by switching field-effect-transistors on and off in said detector panel and photo-conductive charge retention caused by photon signals impinging upon photodiodes in said detector panel.

* * * * *